(12) United States Patent
Baettig et al.

(10) Patent No.: US 7,842,801 B2
(45) Date of Patent: Nov. 30, 2010

(54) PHTHALOCYANINE DYES AND THEIR PREPARATION AND USE

(75) Inventors: Kurt Baettig, Le Mouret (CH); Damien Moigno, Marly (CH)

(73) Assignee: ILFORD Imaging Switzerland GmbH (CH)

( * ) Notice: Subject to any disclaimer, the term of this patent is extended or adjusted under 35 U.S.C. 154(b) by 0 days.

(21) Appl. No.: 12/316,840

(22) Filed: Dec. 17, 2008

(65) Prior Publication Data

US 2009/0155177 A1    Jun. 18, 2009

(30) Foreign Application Priority Data

Dec. 17, 2007    (EP) .................................. 07150050

(51) Int. Cl.
*C07B 47/00* (2006.01)
*C07D 487/22* (2006.01)
*C09D 11/00* (2006.01)

(52) U.S. Cl. .................... 540/145; 540/129; 106/31.49; 347/100

(58) Field of Classification Search ................. 540/129, 540/145; 106/31.49, 49; 347/100; 514/410
See application file for complete search history.

(56) References Cited

U.S. PATENT DOCUMENTS

| 5,484,778 A | 1/1996 | Kenney et al. |
| 2008/0257210 A1 | 10/2008 | Baettig et al. |

FOREIGN PATENT DOCUMENTS

EP    1867685    12/2007

(Continued)

OTHER PUBLICATIONS

Pinedo et al, "Translational Research . . . ", The Oncologist 2000; 5(suppl1); 1-2. [www.The Oncologist.com].*

(Continued)

*Primary Examiner*—James O. Wilson
*Assistant Examiner*—Paul V. Ward
(74) *Attorney, Agent, or Firm*—Onofrio Law; Dara L. Onofrio, Esq.

(57) ABSTRACT

Phthalocyanine dyes of general formula (II)

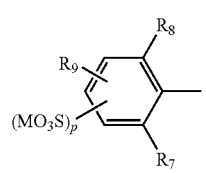

(II)

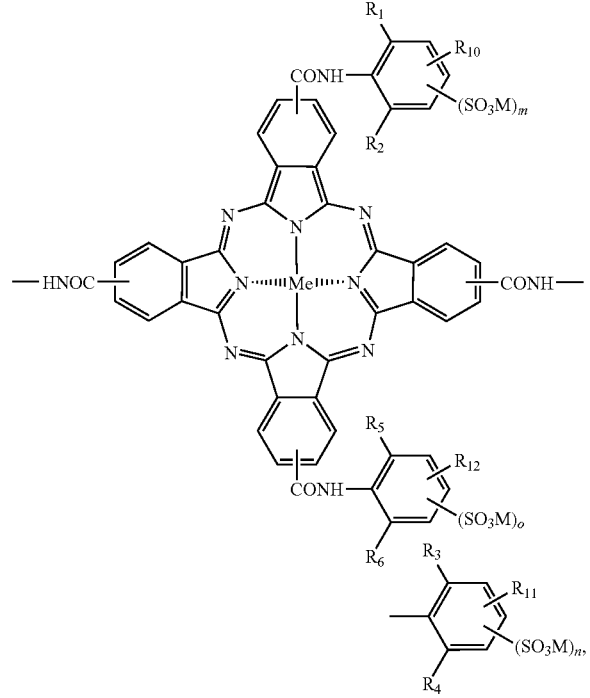

and, in particular, of general formula (III)

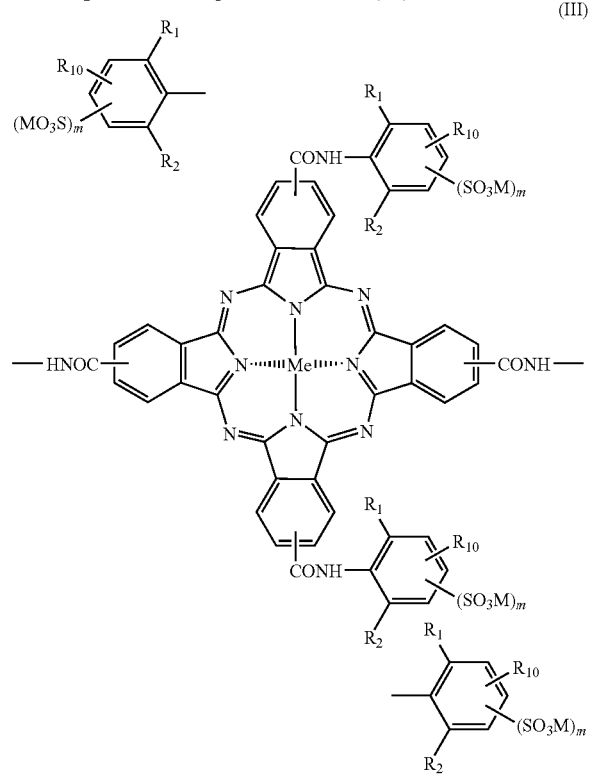

(III)

wherein $R_1$-$R_8$, $R_9$-$R_{12}$, Me, M, m, n, o and p are as described in the specification, are excellent photosensitizers for the preparation of pharmaceutical compositions for photodynamic therapy or photo diagnostics.

9 Claims, 1 Drawing Sheet

FOREIGN PATENT DOCUMENTS

| | | |
|---|---|---|
| JP | 09-249814 | 9/1997 |
| JP | 2003-213153 | 7/2003 |
| WO | WO 92/01753 | 2/1992 |
| WO | WO 95/05818 | 3/1995 |
| WO | WO 95/06688 | 3/1995 |
| WO | WO 02/090361 A1 | 11/2002 |

OTHER PUBLICATIONS

McMahon, G., VEGF Receptor Signaling in Tumor Angiogenisis. The Oncologist 2000;5(suppl 1):3-10. [www.TheOncologist.com].*

C.M. Allen, W.M. Sharman and J.E. Van Lier, "Current status of phthalocyanines in the photodynamic therapy of cancer," Journal of Porphyrins and Phthalocyanines 5, 161-169 (2001).

M. Hannack, H. Heckmann and R. Polley, "Phthalocyanines and Related Compounds" 1998, vol. E 9d of Houben-Weyl, Methods of Organic Chemistry ISBN 3-13-101614-0, pp. 717-842.

J. He, G. Benkö, F. Korodi, T. Polívka, R. Lomoth, B. åkermark, L. Sun, A. Hagfeldt and V. Sundström, "Modified Phthalocyanines for Efficient Near-IR Sensitization of Nanostructured $TiO_2$ Electrode," Journal of the American Chemical Society 124, 4922-4932 (2002).

A.A. Pashkovskaya, E.A. Sokolenko, V.S. Sokolov, E.A. Kotova and Y.N. Antonenko, "Photodynamic activity and binding of sulfonated metallophthalocyanines to phospholipid membranes: Contribution of metal-phosphate coordination," Biochimica et Biophysica Acta 1768, 2459-2465 (2007).

J. Griffiths, J. Schofield, M. Wainwright and S.B. Brown, "Some Observations on the Synthesis of Polysubstituted Zinc Phthalocyanine Sensitisers for Photodynamic Therapy," Dyes and Pigments 33, 65-78 (1997).

L. Bourré, G. Simonneaux, Y. Ferrand, S. Thibaut, Y. Lajat and T. Patrice, "Synthesis, and in vitro and in vivo evaluation of a diphenylchlorin sensitizer for photodynamic therapy," Journal of Photochemistry and Photobiology 69, 179-192 (2003).

G.J.P. Britovsek, G.Y.Y. Woo and N. Assavathorn, "Synthesis and reactivity of water-soluble platinum (II) complexes containing nitrogen ligands," Journal of Organometallic Chemistry 679, 110-115 (2003).

E. Ben-Hur and I. Rosenthal, "The phthalocyanines: a new class of mammalian cells photosensitizers with a potential for cancer phototherapy," International Journal of Radiation Biology 47, 145-147 (1985).

E. Ben-Hur and W.S. Chan, "Phthalocyanines in Photobiology and Their Medical Applications" (2003), Chapter 117 vol. 19, The Porphyrin Handbook, ISBN 0-12-393229-7, pp. 1-35.

* cited by examiner

Figure 1

PHTHALOCYANINE DYES AND THEIR PREPARATION AND USE

FIELD OF THE INVENTION

The invention relates to novel substituted, water-soluble phthalocyanine dyes, their salts, a method of their preparation and their use in pharmaceutical compositions and medicaments for photodynamic therapy and for the treatment of infectious diseases induced by viruses, fungi or microbes, cancer and dermatological diseases.

BACKGROUND OF THE INVENTION

Photodynamic therapy is a method for treatment of tumors and other tissue alterations by light in combination with a light sensitive substance, a so-called photosensitizer, and oxygen contained in the tissue. Such a sensitizer or one of its metabolic precursors is administered to a patient. This sensitizer or metabolic precursor selectively accumulates in the tumor. After a certain waiting time, the tumor and the surrounding healthy tissue are irradiated with light of an appropriate wavelength. Photophysical processes generate toxic substances, so-called reactive oxygen species, from oxygen contained in the tissue. These reactive oxygen species selectively damage the tumor, because the sensitizer has selectively accumulated in the tumor tissue.

In comparison to a surgical treatment, photodynamic therapy has the advantage of a non-invasive or only slightly invasive treatment. In particular, there is no need, for security reasons, for the removal of a large amount of healthy tissue near the tumor. Irradiation with light is from 10 to 100 minutes at a typical light intensity of from 100 mW/cm$^2$ to 100 mW/cm$^2$. The tissue is therefore only slightly heated. Photodynamic therapy of tumors normally needs only a single treatment, it is however possible to repeat the treatment. As light of normal wavelength is used, the impact on the patient is relatively small in comparison to a "classical" treatment.

The disadvantage of photodynamic therapy is the relatively small penetration depth of light of only a few millimeters. Therefore, in most cases, only tumors in the initial stage or of flat shape may be treated effectively. Such tumors suitable for photodynamic therapy are for example skin tumors, such as actinic keratodermia or basalioma, but also warts. The use of lasers and fiber-optic light guides also permits the treatment of tumors inside the body if their surface is accessible by an endoscope.

Photodynamic therapy of tumors inside the body today is only rarely used, in most cases only for palliative purposes in the oesophagus, in cancers of the bile duct or the gall bladder or in brain tumors.

Photodynamic therapy was already investigated in Munich at the beginning of the twentieth century. It came into wider use only in the eighties after improvements of photosensitizers and the use of lasers. Typical ranges of application are the treatment of tumors in the urinary bladder, at the surface of the head, in the oral cavity, in the larynx, in the lung, in the bile duct and in the genital region.

The fundamental physical process of photodynamic therapy has several steps and needs the presence of oxygen that is present in sufficient amounts in most cells. A molecule of the photosensitizer absorbs a light photon and is excited into its first excited singlet state. If the lifetime of this singlet state is long enough, the probability of a transition into the excited triplet state by inter-combination increases. As optical transitions from this excited triplet state into the ground state are very improbable, its lifetime is very long. This allows the contact with many molecules in the surroundings. In the case where it encounters a molecule with a triplet ground state, energy exchange is possible wherein both molecules change into the singlet state. One of the rare molecules with a triplet ground state is molecular oxygen. As the energy of the excited sensitizer molecule is higher than the energy needed for a transition of oxygen into an excited singlet state, such a transition is possible. The excited singlet oxygen has a very long lifetime with respect to an optical transition into its ground state. As the excited singlet oxygen is very reactive, it can damage cell constituents in the vicinity by oxidation. A necrosis is induced or, by an impact on the mitochondria membrane, an aptotose.

In most cases, porphyrins are used as photosensitizers. They are activated by exposure to red light at wavelengths between 630 nm and 635 nm. 5-Aminolevulinic acid or its methyl ester, metabolic precursors of protoporphyrin, are also sometimes used. Protoporphyrin selectively initiates synthesis of porphyrin in tumour cells. Modern photosensitizers may be activated at higher wavelengths with the advantage of a bigger penetration depth of the light into the tissue. Photosensitizers normally show fluorescence and are therefore also used in fluorescence diagnosis of tumors.

Optimal wavelengths for photodynamic therapy are situated between 600 nm and 1500 nm. At shorter wavelengths, the tissue is not transparent enough for the radiation and at longer wavelengths the energy of the radiation is too low. The penetration depth in tissue is 4 mm at a wavelength of 630 nm and 8 mm at a wavelength of 700 nm.

The use of phthalocyanine dyes as photosensitizers in photodynamic therapy was first described by E. Ben-Hur and I. Rosenthal in "The phthalocyanines: a new class of mammalian cells photosensitizers with a potential for cancer phototherapy", International Journal of Radiation Biology 47, 145-147 (1985) and subsequently by C. M. Allen, W. M. Sharman and J. E. van Lier in "Current status of phthalocyanines in the photodynamic therapy of cancer", Journal of Porphyrins and Phthalocyanines 5, 161-169 (2002) and by E. Ben-Hur and W.-S. Chan in "Phthalocyanines in Photobiology and their Medical Applications", Volume 19, pages 1-35 by K. M. Kadish, K. M. Smith and R. Guilard (Editors), "The Porphyrin Handbook", Academic Press San Diego (2003), ISBN 0-12-393229-7. The photodynamic activity and the adsorption of sulphonated phthalocyanines on membranes is described by A. A. Pashkovskaya, E. A. Sokolenko, V. S. Sokolov, E. A. Kotova and Y. N. Antonenko in "Photodynamic activity and binding of sulfonated metallophthalocyanines to phospholipid membranes: Contribution of metal-phosphate coordination", Biochimica et Biophysica Acta 1768, 2459-2465 (2007).

The synthesis of the often-used zinc phthalocyanine dye of formula (I)

(I)

and its photodynamic activity as photosensitizer is described by J. Griffith, J. Schoefield, M. Wainwright and S. B. Brown in "Some observations on the Synthesis of Polysubstituted Zinc Phthalocyanine Sensitizers for Photodynamic Therapies", Dyes and Pigments 33, 65-78 (1997).

Unsubstituted phthalocyanine dyes as photosensitizers for photodynamic therapy are described in patent application WO 92/01,753. The central atom of the phthalocyanine dye is silicium or aluminum.

Unsubstituted phthalocyanine dyes as photosensitizers for photodynamic therapy are also described in patent application WO 95/06,688. The central atom of the phthalocyanine dye is silicium or aluminum.

Unsubstituted phthalocyanine dyes as photosensitizers for photodynamic therapy are also described in U.S. Pat. No. 5,484,778. The central atom of the phthalocyanine dye is silicium.

Substituted phthalocyanine dyes as photosensitizers for photodynamic therapy are also described in patent application WO 95/05,818. The central atom of the phthalocyanine dye is a diamagnetic metal atom or silicium.

Substituted phthalocyanine dyes as photosensitizers for photodynamic therapy are described in patent application WO 02/090,361. The central atom of the phthalocyanine dye is silicium, zinc or aluminum.

An ideal photosensitizer for photodynamic therapy should be highly soluble in the cell medium, non-toxic and very efficient. It should accumulate very selectively only in tumors. In the case where it is toxic, it should be rapidly metabolized to harmless, non-toxic compounds which may easily be eliminated from the body.

There is therefore still a need for improved photosensitizers for photodynamic therapy having these properties. In particular, the absorption maximum of the compounds should be above 630 nm, preferably above 650 nm.

SUMMARY OF THE INVENTION

We have now surprisingly found that novel substituted phthalocyanine dyes have these properties and are therefore ideal photosensitizers for photodynamic therapy.

A further object of the invention is to provide pharmaceutical compositions and medicaments for photodynamic therapy comprising the phthalocyanine dyes according to the invention.

Other objects, features and advantages of the present invention will be apparent when the detailed description of the preferred embodiments of the invention are considered with reference to the drawings, which should be construed in an illustrative and not limiting sense.

DESCRIPTION OF THE INVENTION

Figure 1:
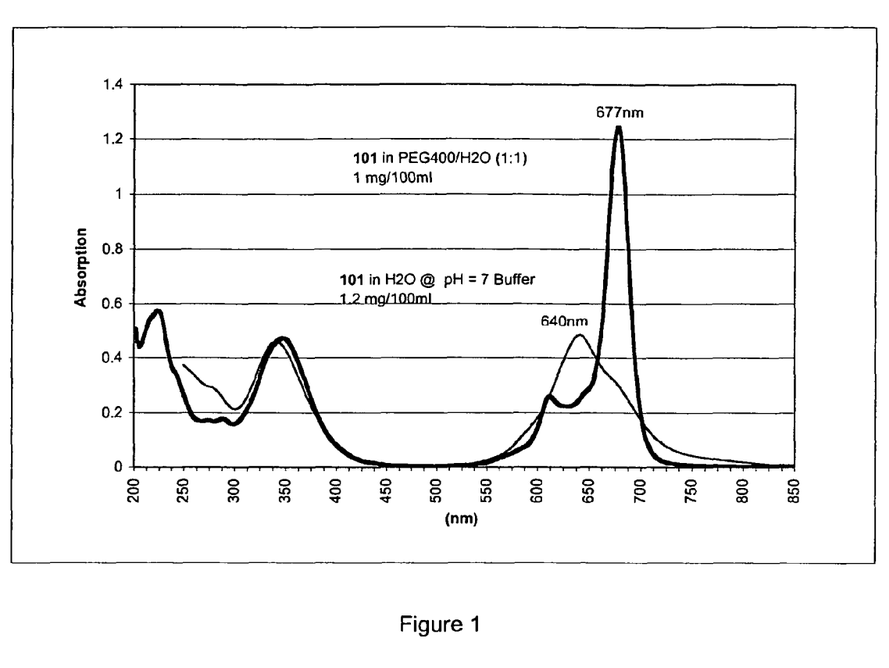
FIG. 1 is the dye normalized absorption spectra of the phthalocyanine dye (100) according to the invention in aqueous solution and in an aqueous solution of polyethylene glycol.

The present invention relates to novel phthalocyanine dyes of general formula (II), wherein $R_1$-$R_8$ independently represent a linear or branched alkyl group having up to 8 carbon atoms;

$R_9$-$R_{12}$ independently represent hydrogen, a linear or branched alkyl group having up to 8 carbon atoms or halogen;

Me represents zinc, magnesium, aluminum, hydrogen, gallium, germanium or tin;

M represents hydrogen, a metal cation or an ammonium cation, which optionally may be substituted by one or more unsubstituted or substituted alkyl or hyxdoxyalkoxyalkyl groups each having from 1 to 12 carbon atoms and m, n, o, p independently are 1 or 2.

Phthalocyanine dyes, wherein m, n, o and p are equal to 1, are preferred.

Phthalocyanine dyes, wherein Me represents zinc, aluminum, magnesium or hydrogen, are also preferred.

Also preferred are phthalocyanine dyes, wherein M represents the cation of the metals sodium, potassium or lithium or an ammonium cation, which is substituted by one or more unsubstituted or substituted alkyl or hyxdoxyalkoxyalkyl groups each having from 1 to 6 carbon atoms.

Particularly preferred are symmetric phthalocyanine dyes of general formula (III), (III)

wherein 4 identical substituents are arranged around the central Me atom. In these dyes, m, n, o and p have the same value. The substituents $R_1$, $R_3$, $R_5$ and $R_7$ are identical, as well as the substituents $R_2$, $R_4$, $R_6$ and $R_8$ and, as well, the substituents $R_9$, $R_{10}$, $R_{11}$ and $R_{12}$. $R_1$, $R_2$, $R_{10}$, Me and m are as defined above.

Symmetric phthalocyanine dyes, wherein m is equal to 1, are preferred.

Symmetric phthalocyanine dyes, wherein Me represents zinc, aluminum, magnesium or hydrogen, are preferred.

Also preferred are the symmetric phthalocyanine dyes, wherein M represents the cation of the metals sodium, potassium or lithium or an ammonium cation, which is substituted by one or more unsubstituted or substituted alkyl or hydroxyalkoxyalkyl groups each having from 1 to 6 carbon atoms.

The invention also relates to a method of preparation of the phthalocyanine dyes of general formula (II) according to the invention, wherein an aromatic amine of general formula (IV A), (IV A)

wherein $R_1$, $R_2$, $R_{10}$ and m are as defined above;

of general formula (IV B), (IV B)

wherein $R_3$, $R_4$, $R_{11}$ and n are as defined above;

of general formula (IV C), wherein $R_5$, $R_6$, $R_{12}$ and o are as defined above; and of general formula (IV D), wherein $R_7$, $R_8$, $R_{12}$ and p are as defined above, are reacted with the acyl chloride of formula (V)

under conditions that the amides of general formulas are formed.

For the preparation of the asymmetrical phthalocyanine dyes of general formula (II), a mixture of the amides (VI A), (VI B), (VI C) and (VI D) is reacted at higher temperatures in an aprotic solvent in the presence of a strong base with a salt of metal Me, if Me does not represent hydrogen.

Particularly preferred aprotic solvents are N-methylpyrrolidone, N-methylacetamide and formamide. Other aprotic solvents having similar properties may also be used.

Suitable metal salts are acetates, nitrates and chlorides.

Suitable strong bases are 1,8-diazabicyclo(4.4.0)undec-7-ene, 1,4-diazabicyclo(2.2.2)octane and other compounds having similar basic properties.

Suitable conditions for this reaction are described for example by M. Hanack, H. Heckmann and R. Polley in "Phthalocyanines and Related Compounds", Volume E 9d, pages 717-842 of Houben-Weyl, "Methods of Organic Chemistry", Georg Thieme editions Stuttgart • New York (1998), ISBN 3-13-101614-0.

The amide of general formula (VI A) is reacted with a salt of metal Me for the preparation of the symmetrical phthalocyanine dyes of general formula (III), if Me does not represent hydrogen.

The following symmetric phthalocyanine dyes of general formula (III) are specific examples, wherein the substituents are as defined in Table 1:

(100)

(101)

-continued

(102)

(103)

-continued (104)

(105)

and

The invention does not only relate to pure phthalocyanine dyes of general formulas (II) and (III), but also to mixtures of these phthalocyanine dyes.

The phthalocyanine dyes of general formulas (II) and (III) according to the invention are very suitable photosensitizers for photodynamic therapy of various tumours and the treatment of microbial and viral infections. They are also very suitable as photodiagnostic agents.

The phthalocyanine dyes according to the invention may be used for destroying cancer tissue, pre-cancerous cell tissue, photo-aged, otherwise damaged or pathologic cells, activated cells such as lymphocytes or other cells of the immune system, and inflamed cells but also for the treatment of viral, fungal or bacterial infection diseases, cancer and dermatological diseases.

The phthalocyanine dyes according to the invention may be activated by light having a wavelength above about 670 nm, which penetrates quite easily into the body tissue.

The hydrophilic properties of the substituents and/or the absorption on hydrophilic carriers may improve the degradation in the body of the phthalocyanine dyes according to the invention. For this reason, the phthalocyanine dyes according to the invention are in vivo rapidly eliminated from the body and the problems relating to toxicity and skin phototoxicity are drastically reduced.

The phthalocyanine dyes of general formulas (II) and (III) according to the invention are preferably used in pharmaceutical compositions and medicaments comprising a pharmaceutical carrier such as a mixture of polyethylene glycol, ethanol and water; polyethylene glycol and water; liposomes, nano containers, biopolymers or other suitable accepted pharmaceutical carriers and suitable diluents.

The pharmaceutical compositions and medicaments comprising the phthalocyanine dyes of general formulas (II) and (III) according to the invention are very suitable as photosensitizing compositions and pharmaceutical products for photodynamic therapy of various tumors and the treatment of microbial and viral infections. They are also very suitable as photodiagnostic agents.

The pharmaceutical compositions and medicaments comprising the phthalocyanine dyes of general formulas (II) and (III) according to the invention may be used for destroying cancer tissue, pre-cancerous cell tissue, photo-aged, otherwise damaged or pathologic cells, activated cells such as lymphocytes or other cells of the immune system, and inflamed cells but also for the treatment of viral, fungal or bacterial infection diseases, cancer and dermatological diseases.

The present invention will be illustrated in more detail by the following examples without limiting the scope of the claimed phthalocyanine dyes in any way.

EXAMPLES

Example 1

The symmetric zinc phthalocyanine dye (100) was prepared in the following way:

6.7 g (30 mmoles) of the aniline of formula (VII), prepared according to the method described by G. P. Britovsek, G. Y. Y. Woo and N. Assavathorn in "Synthesis and reactivity of water-soluble platinum(II) complexes containing nitrogen ligands", Journal of Organometallic Chemistry 679, 110-115 (2003), were suspended in 25 ml of pyridine.

5.7 g (30 mmoles) of the acyl chloride of formula (VIII), (VIII)

prepared according to the method described by J. J. He, G. Benkö, F. Korodi, T. Polívka, R. Lomoth, B. Åkermak, L. Sun, A Hagfeldt and V. Sundström in "Modified Phthalocyanines for Efficient Near-IR Sensitization of Nanostructured TiO$_2$ Electrode", Journal of the American Chemical Society 124, 4922-4932 (2002), dissolved in 8 ml of ethyl acetate, were added drop-wise under ice cooling to this suspension in such a manner that the temperature did not exceed 30° C. After completion of the addition, the reaction mixture was stirred for 18 hours at room temperature. Afterwards, the mixture was diluted with 40 ml of ethyl acetate and the precipitate was suction filtered and purified by recrystallisation in 140 ml of methanol. 7.2 g of the amide of formula (IX) were obtained after drying.

(IX)

7.0 g (16 mmoles) of the amide of formula (IX), 0.88 g (4 mmoles) of zinc acetate dihydrate and 4.0 g of 1,8-diazabicyclo(5.4.0)undec-7-ene in 10 ml of formamide were stirred for 18 hours at a temperature of 110° C. Afterwards, the deep-green solution was cooled down to room temperature, diluted with 30 ml of ethanol, the dye was precipitated as potassium salt by the addition of 5.0 g of potassium acetate and the precipitate was filtered off. 4.0 g of the potassium salt of the phthalocyanine dye (100) were obtained in this way.

In place of 1,8-diazabicyclo(5.4.0)undec-7-ene other strong organic bases such as 1,4-diazabicyclo(2.2.2)octane may be used. In place of potassium acetate, the acetate or chloride of another alkaline metal, such as sodium acetate or lithium chloride, may be used. In this case, the phthalocyanine dye is obtained as sodium or lithium salt.

The symmetric phthalocyanine dyes (101) to (106) according to the invention may be prepared in a similar way by using appropriate quantities of appropriate starting materials.

Example 2

An asymmetric zinc phthalocyanine dye was prepared in the following way:

7.7 g (30 mmoles) of the aniline of formula (X), (X)

prepared according to the method described by G. P. Britovsek, G. Y. Y. Woo and N. Assavathorn in "Synthesis and reactivity of water-soluble platinum(II) complexes containing nitrogen ligands", Journal of Organometallic Chemistry 679, 110-115 (2003), were suspended in 30 ml of pyridine.

5.7 g (30 mmoles) of the acyl chloride of formula (VIII) were added drop-wise under ice cooling to this suspension in such a manner that temperature did not exceeded 30° C. After completion of the addition, the reaction mixture was stirred for 18 hours at room temperature. Afterwards, the mixture was diluted with 20 ml of N-methylpyrrolidone and 20 ml of ethyl acetate, filtered and concentrated. The raw product was purified by stirring in 50 ml of a saturated solution of sodium chloride. 6.7 g of the amide of formula (XI) were obtained after drying.

(XI)

3.5 g (8 mmoles) of the amide of formula (X) and 3.9 g (8 mmoles) of the amide of formula (XI), 0.8 g (4 mmoles) of zinc acetate dihydrate and 2.4 g of 1,8-diazabicyclo(5.4.0) undec-7-ene in 10 ml of formamide were stirred for 18 hours at a temperature of 110° C. Afterwards, the deep-green solution was cooled down to room temperature, diluted with 30 ml of ethanol, the dye was precipitated as potassium salt by the addition of 5.0 g of potassium acetate and the precipitate was filtered off. 3.0 g of the potassium salts of a mixture of phthalocyanine dyes were obtained in this way.

This mixture of zinc phthalocyanine dyes contains, besides other dyes, the zinc phthalocyanine dye of formula the zinc phthalocyanine dye of formula 30 the zinc phthalocyanine dye of formula 65 and the zinc phthalocyanine dye of formula

In the four preceding formulas, Me represents zinc.

Tests

1. Light Absorption in Aqueous Solution

The absorption spectrum in aqueous solution was measured at a concentration of 20 mg/l to 30 mg/l of the phthalocyanine dye in an optical cuvette of 1 cm thickness with a spectrometer Cary 100 Bio UV/VIS (available from Varian Inc., Palo Alto, USA) in a buffered aqueous solution at a value of pH of 7.0.

The phthalocyanine dyes aggregate in aqueous solution. The absorption maximum is therefore that of the formed aggregate.

2. Light Absorption in an Aqueous Solution of Polyethylene glycol

The absorption spectrum was measured at a concentration of 20 mg/l to 30 mg/l of the phthalocyanine dye in an optical cell of 1 cm thickness with a spectrometer Cary 100 Bio UV/VIS in a buffered aqueous solution containing 50 percent by weight of polyethylene glycol 400 at a value of pH of 7.0.

The phthalocyanine dyes only slightly aggregate in an aqueous solution of polyethylene glycol. The absorption maximum is therefore that of the monomer phthalocyanine dye. This absorption maximum is at a higher wavelength than that of the phthalocyanine dye aggregate.

3. Light Absorption in Presence of Fetal Calf Serum

The absorption spectrum was measured with a spectrometer Cary 100 Bio UV/VIS between 300 nm and 800 nm. 1 mg of the phthalocyanine dye was dissolved in a solution of polyethylene glycol 400, ethanol and water (30:20:50). The resulting solution was diluted with a physiological salt solution, containing fetal calf serum at a concentration of 10%, to a concentration of 10 µg/ml. This solution containing fetal calf serum simulates the biological conditions in the cell interior.

In the solution containing fetal calf serum, phthalocyanine dyes particularly well suited for photodynamic therapy show a high ratio of the absorption in the absorption maximum of the monomer form and the absorption in the absorption maximum of the aggregated form of the phthalocyanine dye.

4. Photodynamic Activity

The phthalocyanine dyes were tested for their photodynamic activity by using the method described by L. Bourré, G. Simonneaux, Y. Ferrand, S. Thibaut, Y. Lajat and T. Patrice in "Synthesis, and in vitro and in vivo evaluation of a diphenyl-chlorin sensitizer for photodynamic therapy", Journal of Photochemistry and Photobiology B: Biology 69, 179-192 (2003).

In this method, cells of type HT29 that are very resistant against photodynamic therapy (human adenocarcinoma cells, ECACC No. 91072201, available from CERDIC, Sophia-Antipolis, France) and of type F98 were prepared for the test on photodynamic therapy in cell culture medium RPMI 1640 by a method known to someone skilled in the art (see paragraph 2.2.3 of the cited article). 24 hours later, the cells were incubated with the phthalocyanine dye at concentrations up to 10 µg/ml for 4 hours. Afterwards, the cells were exposed through an optical fiber to 20 J/cm$^2$ of radiation energy using a tunable laser CR 599 (available from Coherent Laser Group, Santa Clara, USA). The number of cells surviving the photodynamic therapy was determined by the MMT ([3-(4,5-dimethlylthiazol-2-yl)-2,5-diphenyltetrazolium bromide], available from Sigma-Aldrich Chemie GmbH, Buchs, Switzerland) colorimetric method.

The amount of radiation corresponds more or less to the amount of 200 J/cm$^2$ of radiation normally used in vivo in photodynamic therapy of human tissue.

5. Reactive Oxygen Species

The amount of reactive oxygen species generated during exposure to light was determined in the following way:

The phthalocyanine dye was dissolved in an aqueous solution (10%) of foetal calf serum at a concentration of 10 µg/ml. Luminol (3-phthalhydrazide, available from Sigma-Aldrich Chemie GmbH, Buchs, Switzerland) was dissolved in a 0.1 molar phosphate buffer solution at a concentration of 0.5 mg/l at a value of pH of 12.4. 1 ml of the solution of luminol was poured into a quadratic spectrofluorometer cuvette of edge length 1 cm containing the solution of the phthalocyanine dye. Afterwards, the cuvette was irradiated with 10 J/cm$^2$ of light at the absorption maximum of the phthalocyanine dye a temperature of 30° C. Reactive oxygen species are generated that oxidize luminol to fluorescent aminophthalic acid with an absorption maximum at 485 nm. The fluorescence spectrum of this solution, after excitation of the aminophthalic acid with light of wavelength 395 nm, was measured with a fluorescence spectrometer Cary PCB 150 (available from Varian Inc., Palo Alto, USA) 15 minutes after the end of irradiation. The amount of generated reactive oxygen species is proportional to the difference measured fluorescence of the irradiated test cuvette and of an irradiated comparison cuvette not containing the phthalocyanine dye. The most reactive phthalocyanine dyes show the highest value (arbitrary units).

Results

The measured absorption maximum of the phthalocyanine dyes according to the invention having different metals Me and different metal cations M are presented in Table 1.

TABLE 1

| Dye No. | Me | M | $\lambda_{max}$ in H$_2$O (nm) | $\lambda_{max}$ in H$_2$O/PEG 400 (nm) |
|---|---|---|---|---|
| 100 | Zn | K | 628 | 687 |
| 101 | Zn | Na | 638 | 685 |
| 101 | Al | K | 694 | 683 |
| 101 | Mg | K | 641 | 688 |
| 101 | H | K | 608 | 639, 677 |
| 102 | Zn | K | 638 | 685 |
| 103 | Zn | K | 623 | 685 |
| 104 | Zn | K | 625 | 685 |
| 105 | Zn | K | 633 | 685 |
| 106 | Zn | Li | 681 | 685 |
| I | Zn | H | 611 | 678 |

The absorption maximum of dye (106) was measured in a 1:1 mixture of water and ethanol.

The phthalocyanine dye of formula (I) is available from Frontier Scientific, Logan, USA.

A comparison of the absorption maxima of Table 1 in both solutions clearly shows that the phthalocyanine dye (100) to (106) according to the invention and the phthalocyanine dye of formula (I), representing the state of the art, show the aggregate form in aqueous solution and the monomer form in the aqueous solution of polyethylene glycol.

The results of the measurements of light absorption in the presence of foetal calf serum of the phthalocyanine dye (101) according to the invention and of the phthalocyanine dye of formula (I), representing the state of the art, both in a concentration of 10 µg/ml, are listed in Table 2. The ratio of the absorption in the absorption maximum of the monomer form of the phthalocyanine dye and the absorption in the absorption maximum of the aggregate form of the phthalocyanine dye is given.

TABLE 2

| Dye No. | Absorption ratio |
|---|---|
| 101 | 0.79 |
| I | 0.58 |

A comparison of the values in Table 2 clearly shows that the phthalocyanine dye (101) according to the invention has, for the photodynamic therapy, a more suitable ratio of the absorption in the absorption maximum of the monomer form of the phthalocyanine dye and the absorption in the absorption maximum of the aggregate form of the phthalocyanine dye in comparison to the phthalocyanine dye of formula (I) representing the state of the art.

The results of the measurements of photodynamic activity after irradiation at the absorption maximum of the monomer zinc phthalocyanine dye (101) according to the invention and of the phthalocyanine dye of formula (I), representing the state of the art, both in a concentration of 10 µg/ml, are listed in Table 3.

TABLE 3

| Dye No. | Cell line | Percentage of surviving cells |
|---|---|---|
| 101 | HT 29 | 12% |
| I | HT 29 | 70% |
| 101 | F 98 | 18% |
| I | F 98 | 84% |

The results in Table 3 immediately show that for both cell lines considerably less cells survive in the case where the phthalocyanine dye (101) according to the invention is used in comparison to the case where the phthalocyanine dye of formula (I), representing the state of the art, is used. The zinc phthalocyanine dye (101) according to the invention has therefore a considerably higher photodynamic activity in comparison to the phthalocyanine dye of formula (I) representing the state of the art.

The results of the determination of the amount of formed reactive oxygen species of the zinc phthalocyanine dye (101) according to the invention and of the phthalocyanine dye of formula (I), representing the state of the art, are listed in Table 4.

TABLE 4

| Dye No. | Irradiation wavelength (nm) | Amount of reactive oxygen species (arbitrary units) |
|---|---|---|
| 101 | 632 | 4.71 |
| 101 | 683 | 5.12 |
| (I) | 675 | 3.51 |

The results in Table 4 immediately show that phthalocyanine dye (101) according to the invention generates considerably more reactive oxygen species in comparison to the phthalocyanine dye of formula (I), representing the state of the art, even in the case where the irradiation is made in the absorption maximum of the aggregated form of the phthalocyanine dye (101).

The foregoing description of various and preferred embodiments of the present invention has been provided for purposes of illustration only, and it is understood that numerous modifications, variations and alterations may be made without departing from the scope and spirit of the invention as set forth in the following claims.

The invention claimed is:

1. A photodynamic therapy method using a photosensitizer comprising a pharmaceutical carrier and one or more phthalocyanine dyes of general formula (II)

(II)

wherein
$R_1$-$R_8$ independently represent a linear or branched alkyl group having up to 8 carbon atoms;
$R_9$-$R_{12}$ independently represent hydrogen, a linear or branched alkyl group having up to 8 carbon atoms or halogen;
Me represents zinc, aluminum, magnesium, hydrogen, gallium, germanium or tin;
M represents hydrogen, a metal cation or an ammonium cation, which optionally may be substituted by one or more unsubstituted or substituted alkyl or hydroxyalkoxyalkyl groups each having from 1 to 12 carbon atoms;
and
m, n, o, p independently are 1 or 2;
wherein said photosensitizer is used to treat cancer;
comprising the steps of administering an effective amount of said photosensitizer to detect the cancer;
and applying light of sufficient wavelength to activate said phthalocyanine dye.

2. The method according to claim 1, wherein said wavelength of light is above 670 nm.

3. The method according to claim 1, wherein said pharmaceutical carrier is hydrophilic.

4. The method according to claim 1, wherein said pharmaceutical carrier is a mixture of polyethylene glycol, ethanol and water.

5. The method according to claim 1, wherein said pharmaceutical carrier is polyethylene glycol and water.

6. The method according to claim 1, wherein said pharmaceutical carrier is selected from the group consisting of liposomes, nano containers and biopolymers.

7. The method according to claim 1, wherein
$R_1$-$R_8$, $R_9$-$R_{12}$, Me and M of said phthalocyanine are as defined in claim 1
and
m, n, o, p are equal to 1.

8. The method according to claim 1, wherein said phthalocyanine dyes is of general formula (III) according to claim 1, (III)

wherein
$R_1$, $R_2$, $R_{10}$, Me, M and m are as defined in claim 1.

9. The method according to claim 8, wherein $R_1$-$R_2$ independently represent a linear or branched alkyl group having up to 8 carbon atoms;

$R_{10}$ represents hydrogen, a linear or branched alkyl group having up to 8 carbon atoms or halogen;

Me represents zinc, aluminum, magnesium, hydrogen, gallium, germanium or tin;

M represents hydrogen, a metal cation or an ammonium cation, which optionally may be substituted by one or more unsubstituted or substituted alkyl or hydroxyalkoxyalkyl groups each having from 1 to 12 carbon atoms;

n, o, p independently are 1 or 2,
and
m is equal to 1.

* * * * *